United States Patent

Andersen

(10) Patent No.: US 9,057,717 B2
(45) Date of Patent: Jun. 16, 2015

(54) AQUATIC POLLUTION MONITORING

(75) Inventor: Odd Ketil Andersen, Stavanger (NO)

(73) Assignee: Biota Tools AS, Stavanger (NO)

( * ) Notice: Subject to any disclaimer, the term of this patent is extended or adjusted under 35 U.S.C. 154(b) by 131 days.

(21) Appl. No.: 13/512,285

(22) PCT Filed: Nov. 26, 2010

(86) PCT No.: PCT/GB2010/051977
§ 371 (c)(1),
(2), (4) Date: Oct. 11, 2012

(87) PCT Pub. No.: WO2011/064595
PCT Pub. Date: Jun. 3, 2011

(65) Prior Publication Data
US 2013/0019811 A1    Jan. 24, 2013

(30) Foreign Application Priority Data
Nov. 27, 2009 (GB) .................................. 0920796.0

(51) Int. Cl.
*A01K 61/00* (2006.01)
*G01N 33/18* (2006.01)
*G01N 21/47* (2006.01)

(52) U.S. Cl.
CPC .......... *G01N 33/186* (2013.01); *G01N 21/4788* (2013.01)

(58) Field of Classification Search
CPC ...... A01K 61/002; A01K 61/00; A23K 1/188
USPC ......... 119/234, 200, 204, 207–211, 238–240;
73/53.01–53.07, 73, 54.01–54.09,
73/54.11–54.19, 54.21–54.29,
73/54.31–54.39, 54.41–54.43, 60.11,
73/61.41–61.49, 61.51–61.59,
73/61.61–61.69, 61.71–61.79,
73/64.41–64.49, 64.51–64.56
See application file for complete search history.

(56) References Cited

U.S. PATENT DOCUMENTS

| 5,628,904 A * | 5/1997 | Bean .............................. 210/602 |
| 6,119,630 A * | 9/2000 | Lobsiger et al. .............. 119/238 |
| 2013/0118236 A1* | 5/2013 | Andersen ..................... 73/61.41 |

FOREIGN PATENT DOCUMENTS

| WO | 2007/086754 A1 | 8/2007 |
| WO | 2009/013503 A1 | 1/2009 |

OTHER PUBLICATIONS

S. Nicholson and P.K.S. Lam, "Pollution monitoring in Southeast Asia using biomarkers in the mytilid mussel *Perna viridis* (Mytilidae: Bivalvia)," Environmental International, 2005, pp. 121-132, vol. 31, Elsevier Ltd.

(Continued)

*Primary Examiner* — Trinh Nguyen
(74) *Attorney, Agent, or Firm* — Hall Estill Attorneys at Law

(57) ABSTRACT

A method of monitoring the effect of pollution in an aquatic mass, said method comprising disposing in said aquatic mass a biosensor unit containing a living sessile organism which exhibits apical growth and which is bound to a carrier, directing an electromagnetic beam towards a corresponding detector and between an edge and the apical tip of said sessile organism whereby to produce a diffraction pattern, detecting said diffraction pattern using said detector and monitoring a change (e.g. successive changes) in said diffraction pattern over time which is indicative of the natural growth of the apical tip of said organism.

13 Claims, 1 Drawing Sheet

(56) References Cited

OTHER PUBLICATIONS

Figure 1:
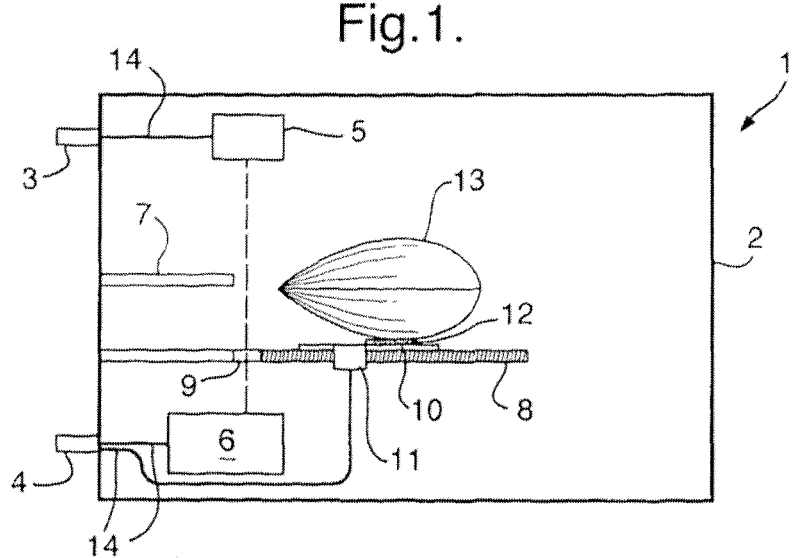

T. Stromgren, "Linear Measurements of Growth of Shells Using Laser Diffraction," Limnology and Oceanography, Jan. 1, 1975, pp. 845-848, vol. 20, No. 5, Grafton, WI, US.

T. Stromgren, "The Combined Effect of Copper and Hydrocarbons on the Length Growth of *Mytilus edulis*," Marine Environmental Research, Jan. 1, 1986, pp. 251-258, vol. 19, No. 4, Elsevier Applied Science Publishers, GB.

S. Lefloch, et al., "Effects of Oil and Bioremediation on Mussel (*Mytilus edulis* L) Growth in Mudflats," Environmental Technology, Oct. 1, 2003, pp. 1211-1219, vol. 24, No. 10, Selper Ltd., GB.

A. R. Manley, et al., "The Effect of Copper and Zinc on the Shell Growth of *Mytilus edulis* Measured by a Laser Diffraction Technique," Journal of the Marine Biological Association of the United Kingdom, Jan. 1, 1984, pp. 417-427, vol. 64, No. 2, Cambridge University Press, GB.

P. C. Almada-Villela, et al., "The Effects of Temperature on the Shell Growth of Young *Mytilus edulis*," Journal of Experimental Marine Biology and Ecology, Jan. 1, 1982, pp. 275-288, vol. 59, No. 2-3, Elsevier Biomedical Press, Amsterdam, NL.

LL. D. Gruffydd, et al., "The Reduction Growth of *Mytilus edulis* in Fluctuatingi Salinity Regines Measured Using Laser Diffraction Patterns and the Exaggeration of This Effect by Usinig Tap Water as the Diluting Medium," Journal of the Marine Biological Association of the United Kingdom, Jan. 1, 1984, pp. 401-409, vol. 64, No. 2, Cambridge University Press, GB.

H. Sushko, et al., "The Use of Laser Diffraction in Measuring the Effect of Suspended Sediment on the Shell Growth of Mussels *Mytilus edulis*," Canadian Manuscript Report of Fisheries and Aquatic Sciences, Jan. 1, 1991, 31 pps., No. 2121, CA.

T. Stromgren, et al., "Growth in Length of *Mytilus edulis* Fed on Different Algal Diets," Journal of Experimental Marine Biology and Ecology, Jan. 1, 1984, pp. 23-34, vol. 76, No. 1, Elsevier, Amsterdam, NL.

"Coral Growth: Lawer Based Underwater and Laboratory Measurements," http://www.aims.gov.au/pages/laser2.html, (page accessed Nov. 21, 2007).

R. Vago, et al., "Laser measurements of coral growth," Nature 386, 1997, pp. 30-31.

T. Stromgren, "Growth Rates of *Modiolus americanus* (Leach) in Relation to Mechanical Disturbance and Darkness," Bulletin of Marine Science 26(3), 1976, pp. 410-413.

T. Stromgren, "Temperature-length Growth Strategies in the Lottoral Alga *Ascophyllum nodosum* (L)," Limnology and Oceanography 28(3), 1983, pp. 516-521, The American Society of Limnology and Oceanography, Inc.

T. Sgromgren, "Skeleton Growth of the Hydrocoral Millepora Complanata Lamarck in Relation to Light," Limnology and Oceanography 21(1), 1976, pp. 156-160.

S. Nixon, "Science: Laser Sheds Light on How Coral Grows," New Scientist magazine, Mar. 8, 1997, p. 16.

\* cited by examiner

AQUATIC POLLUTION MONITORING

This invention relates to improvements in and relating to methods of monitoring pollution in an aquatic mass, and to apparatus for use in such methods.

Pollution of aquatic masses, e.g. oceans, seas, lakes and rivers, may arise through an accidental spill, or as a consequence of a deliberate discharge either of which take the form of the release into the aquatic mass of chemicals which affect the ability of the indigenous flora and fauna to thrive. In the case of deliberate discharges, these may be legally permitted but nonetheless eventually prove unexpectedly to be harmfully. In the case of fixed installations which may be liable to be alleged to be a pollution source, as well as for operators of fixed installations which may suffer detrimental effects from aquatic pollution, it is desirable for the aquatic mass to be monitored to detect pollution events in order that compensatory or protective action may be taken or in order to demonstrate that in fact legal compliance has been achieved. Such installations will typically comprise offshore drilling or hydrocarbon recovery installations, ports and other land/water material transfer locations, land-based industrial, municipal, and private discharges, fish farms and the like. Pollution detection can also be helpful in identifying previously unknown side-effects of legal discharges.

Many multi-cellular non-mammalian aquatic animals, e.g. fish, shellfish, etc. exhibit detectable changes in behaviour in response to exposure to pollution which are far more sensitive than simply measuring death. Such behaviour includes alteration of growth rate, alteration of heart beat, alteration in shell opening and closing behaviour, and changes in siphon behaviour. The use of such animals, so-called "indicator" or "sentinel" species, in real time environmental monitoring (RTEM) methods is widely known and is described for example in WO 2007/086754 and WO 2009/013503, the contents of which are incorporated herein by reference. An important advantage of RTEM methods is that they are non-invasive.

Two systems have evolved which have been used on marine organisms, one based on physiological responses (heart rate monitoring), the other based on behaviour (valve gaping in mussels). However, such systems are most responsive to acute incidents rather than long term, low dose responses. There still exists a need to develop RTEM methods that can directly measure important parameters used in environmental risk assessment and management and which will reduce the use of invasive methods as biomarkers in environmental monitoring. The present invention seeks to address this need and, in particular, to provide alternative methods of directly monitoring aquatic animals which can be used to monitor pollution both in the short and longer term.

Measurements of growth is a central and sensitive parameter in environmental risk assessment. In terms of animal growth as an indicator of pollution, measurement of apical growth (i.e. growth along a defined axis) is particularly appropriate. Apical growth includes, for example, shell size growth of sessile organisms, especially filter feeders such as bivalves (e.g. mussels, clams and scallops) or of predatory organisms, such as barnacles. Also preferable as an indicator of pollution is coral growth. In fact, measurement of growth of any sessile marine organism which possesses apical growth is appropriate in terms of an indicator of pollution, i.e. any marine organism with a defined growth zone. Other organisms which can function as indicator species include plants, e.g. seaweed.

However, while these measurements can be carried out in the laboratory with ease, automated monitoring of shell growth in situ within the aquatic mass being monitored is less straightforward. The use of RTEM in the sea provides additional challenges with regard to in situ deployment due to its corrosive environment. Nonetheless, we have now found that RTEM may effectively be carried out on various marine organisms, such a bivalves, using methods which involve light diffraction. In particular, it has been found that changes in diffraction patterns which are dependent on the separation of an organism which exhibits apical growth and an adjacent structure (edge) can be used to measure apical growth of the organism. This in turn is able to provide a direct indication of aquatic pollution.

Thus viewed from one aspect the invention provides a method of monitoring the effect of pollution in an aquatic mass, said method comprising disposing in said aquatic mass a biosensor unit containing a living sessile organism which exhibits apical growth and which is bound to a carrier, directing an electromagnetic beam towards a corresponding detector and between an edge and the apical tip of said sessile organism whereby to produce a diffraction pattern, detecting said diffraction pattern using said detector and monitoring a change (e.g. successive changes) in said diffraction pattern over time which is indicative of the natural growth of the apical tip of said organism.

Viewed from a second aspect the invention provides a biosensor unit for immersion in an aquatic mass comprising a carrier having a living sessile organism which exhibits apical growth bound thereto, an edge so as to form a gap between it and a tip of the sessile organism, an electromagnetic source arranged such that a beam therefrom impinges upon said gap to produce a diffraction pattern, and a corresponding electromagnetic detector arranged to detect said diffraction pattern and means for monitoring a change (e.g. successive changes) in said diffraction pattern over time which is indicative of the natural growth of the apical tip of said organism. The invention also extends to such a biosensor without the sessile organisms being present.

Thus in accordance with the invention when the gap between the edge and the apical tip of the sessile organism (e.g. the tip of its shell) is sufficiently small, electromagnetic radiation passing through to the detector will form a diffraction pattern (when the diameter of the gap is of the order of the wavelength of the incident light). This in turn will be noticeable above the background light detected by the detector, e.g. as spikes or 'maxima' in the spatial radiation intensity detected across the detector. As the organism grows and the gap is narrowed so the diffraction pattern changes—the maxima become more widely separated. Such changes can be related to the change in slit width and thus the extent of growth of the sessile organism. Thus in turn can be related to the presence or concentration of pollution in the aquatic mass.

Any suitable electromagnetic radiation source can be employed depending upon the sensitivity required. In preferred embodiments the source is a light source although it need not be in the visible range—e.g. the source may have a wavelength between 10 nm and 10 microns, preferably between 300 nm and 800 nm. Unless otherwise specified the term "light" as used herein is not to be taken as limiting the invention to any particular wavelength range.

In preferred embodiments the source is monochromatic in order to make the diffraction pattern as clear as possible. Preferably the source is coherent, preferably comprising a laser. A laser diode or any other suitably compact laser cavity could be employed. Suitable light for use in the invention may be generated by a low energy laser such that there is no harmful effect on the organism. A Ne—He gas laser with a wavelength of 632.7 nm is particularly suitable.

Apical tip growth can be monitored with the carrier in a stationary position until the sessile organism has grown sufficiently for the slit between the apical tip and edge to decrease sufficiently that the diffraction pattern is no longer detectable (either because it has become too faint or the central maximum has expanded to cover the whole detector surface). In some embodiments the carrier and edge are moveable relative to one another in order that the slit can be re-enlarged until a diffraction pattern appears once more. The sessile organism again grows to decrease the slit sufficiently to cause a change in the diffraction pattern and, ultimately, to cause the diffraction pattern to no longer be detectable. If, in successive temporally spaced determinations, the distance between the edge and the apical tip are determined, then these correlate to the apical tip growth (e.g. shell growth) between the temporally spaced determinations.

In carrying out the method of the invention, it is preferred that the apical tip of the sessile organism is initially disposed at a pre-determined distance from the edge such that the resulting slit diameter provides a predetermined diffraction pattern. This could be a diffraction pattern having a pre-defined number of maxima/minima, a predetermined intensity for any given maximum, a predetermined contrast ratio between any maximum and any minimum etc, or indeed any combination of these. The width of the slit formed between the edge and the apical tip which provides such a diffraction pattern will vary depending on factors such as the wavelength of light which is used, the separation of the slit and the sensor, etc. but may readily be determined by those skilled in the art. Typical widths (edge to apical tip separation) which may provide the predetermined diffraction pattern may lie in the range 100 to 900 μm.

Advantageously, the method of the invention enables long term growth of the sessile organism to be monitored. As described above, in a set of embodiments, this may be achieved by disposing the organism or edge on a movable carrier which can be moved away from the edge or organism respectively in order to carry out further diffraction measurements over any desired period (e.g. several days, months, etc.). The carrier could be moved away from the edge when the separation between the apical tip of the organism and the edge has reduced below a predetermined threshold e.g. less than 200 μm (note that in order not to damage the edge, it is preferred that the apical tip and the edge should not physically come into contact with one another) or at predetermined time intervals, which may be dependent on time of year or on previously measured growth rates. Equally movement of the carrier could be prompted simply by the separation becoming too small to give a detectable diffraction pattern. Preferably movement of the carrier is carried out automatically. The length of time taken for the organism to grow sufficiently that the diffraction pattern diminishes will depend on the nature of the organism, the extent of any pollution, etc. In the case of bivalves, such as mussels, this may be expected to take in the region of 1-2 months.

In a preferred embodiment, the method of the invention thus further comprises the step of moving said organism and said edge away from one another when the diffraction pattern is no longer detectable. Preferably, the organism and edge are separated until the detector detects once more a diffraction pattern, preferably a predetermined diffraction pattern as herein defined.

It will generally be preferred to monitor apical tip growth at regular intervals rather than continuously. For example, measurements may be taken at pre-determined time intervals, for example, daily, every 12 hours or, in some cases, more frequently than this, e.g. hourly. The time intervals can be adjusted as required depending on the considered risk of pollution.

Sessile organisms suitable for use in the invention include bivalves, such as mussels, scallops, clams, etc. Where bivalves are used, apical growth is typically measured at the apex (lip) of the shell. Other points of apical growth may include, for example, the top rim of a barnacle. Sessile organisms which do not possess shells, e.g. coral, seaweed, etc. are also suitable for use in the methods herein described. Preferably the sessile organism of which growth is to be measured is a young individual in the growth phase.

Organisms which possess shells may be mounted on the carrier using known methods, e.g. using non-toxic adhesive, cement, filament tape, etc. If apical growth of sessile organisms which do not possess shells is to be measured, known methods may be used to secure the organisms in place, e.g. living algae can be clamped in position on a carrier and coral can be attached to a carrier with filament tape The detector used may comprise any convenient apparatus which is able to detect the spatial distribution of the light or other radiation. Where visible or near-visible light is used a charge-coupled-device (COD) could be used. As an alternative a sweeping or scanning arrangement could be employed. This gives the potential for a greater field of view and thus permits smaller gaps to be observed which in turn allows greater precision in the measurement of the apical growth of the organism. For example the detector could be moveable in a direction parallel to the radiation beam. Alternatively it may take the form of a static, detector with a moving reflector positioned between it and the light source, e.g. an oscillating mirror. In order to enhance the sensitivity to relatively faint non-zero order diffraction maxima it may be desirable in some embodiments to suppress the zero-order maximum either physically with a beam stop (e.g. a light absorber or reflector) or in the detector.

A diverging lens can optionally be included in the path of the diffracted light to allow a shorter distance between the gap and the detector for a given detector resolution.

The edge referred to will be provided by an inert surface up to which the apical tip may grow so as to narrow the gap between apical tip and edge. The edge is preferably provided by a blade, e.g. a narrow sheet positioned at least partially and preferably substantially perpendicular to the light path from light source to light detector (or deflector if a deflector is used). The blade may comprise any suitable material, but typically may be made from a non-corrosive material, such as plastic.

In a set of preferred embodiments, the sessile organism is mounted on a carriage movable towards or away from the edge, e.g. under the influence of a drive motor. The distance the carriage is moved away from the edge may be determinable. This can be achieved in many ways, for example by the use of a threaded screw and a corresponding threaded nut with one attached to the drive motor—the number of rotations required defines the distance moved. Alternatively, a toothed track and a cooperative rotatable cog wheel could be used or a hydraulic system with a control pump. Such mechanical components of the biosensor are preferably provided in a dry (i.e. water-free) part of the system e.g. with a hydraulic connection to the carriage on the outside.

Although the methods herein described may be performed on a single organism, it is preferred that these are carried out simultaneously or sequentially on a plurality of organisms from the same species. In this way, accuracy of the monitoring methods may be improved by measuring the growth rate of a statistically significant sample. In such embodiments a common radiation source and/or detector are preferably employed. For example the apparatus could be arranged to bring a radiation-and-detector arrangement into successive mutual alignment with each of a plurality of organisms.

In an exemplary such embodiment, a plurality of sessile organisms may be distributed around the rim of a disk or the outer surface of a cylinder, each with a corresponding radially separated edge. In this embodiment, each organism may be bound to a movable carriage. The light source may then be distributed between each gap via the use of one or more optical fibres. Where a single optical fibre is used to deliver the light, this should be mounted in such a way that this can be manipulated (either manually or, more preferably, automatically) to successively distribute the light beam between each gap. Preferably, the growth of a statistically significant sample is measured, especially preferably 4-20 organisms, particularly 5-10, e.g. 8.

To allow for bivalve growth in other dimensions than shell tip growth, where necessary a further drive mechanism may be provided to allow the shell tip to be aligned with the edge. Cameras can be used to monitor shell position, and the further drive mechanism then operated to achieve the desired alignment.

To ensure a bivalve shell is closed during shell tip growth measurements, the apparatus used is preferably provided with means to induce shell closing, for example a noise, water motion or vibration generator, which may be activated shortly before measurements are made. A camera can be used to observe opening and closing of the shell.

To avoid disturbance from any light scattering particles present it is preferable to filter the water in the cage before carrying out measurements.

Furthermore, methods herein described may further comprise additional means of monitoring other motion of the organisms, for example shell opening and closing and heart beat using methods known in the art.

As time progresses, new sessile organisms may be required and so the apparatus used is preferably configured such that the organism(s) is/are provided on a replaceable module.

In some embodiments the apparatus includes a water sampler so that retrieval of a unit also allows retrieval of temporally spaced water samples for later chemical or biochemical analysis. Such units may readily be cleaned, refitted with a fresh sessile organism and reinstalled.

The apparatus could be provided on any suitable structure depending upon how it is intended to be employed. In some embodiments the components of the apparatus are housed in a water-pervious cage.

The data collected in the biosensor unit could be stored locally for subsequent retrieval but preferably the apparatus comprises data transmission means for transmitting said date to a remote receiver. Any suitable method of data transmission could be employed e.g. a cable, radio, microwave, sonar transmission. The remote receiver typically comprises a computer, e.g. one on or in the installation being monitored. The computer is desirably arranged to generate a signal indicative of the occurrence or non-occurrence of a pollution event. That signal may be generated using signals from the biosensor unit, optionally combined with signals from other sensors, e.g. sensors on or in the installation being monitored.

The sensor unit is preferably also provided with at least one of the following monitors: a temperature monitor; a light monitor; a sound monitor; a salinity monitor; an alkalinity monitor; and a water-flow monitor. The unit preferably also comprises anchoring means and signal transmission means, e.g. a data cable or a radio transmitter.

It is particularly preferred that a plurality of such sensor units be used to monitor an installation and that these be arranged around the installation (if offshore), offshore of the installation (if on shore) or in a freshwater lake or river. Desirably such sensor units are placed upstream and downstream of the installation. Also desirably such sensor units may be arranged both near surface and near bed (i.e. near sea-bed, lake-bed, river bed, etc.).

The signal generated by the computer indicative of the occurrence or non-occurrence of a pollution event may be continuous, regular or on occasion of an event. Moreover, it may be quantitative, semi-quantitative or qualitative. Thus for example it may simply indicate that current conditions are normal, that a specific event has occurred, or that an ongoing discharge is in fact having an effect on the environment. Desirably the signal will indicate the timing, severity and location of an event or the severity of the environmental impact of a discharge. In this way, the installation operator or the monitor of the installation's operations is alerted to take action, e.g. to discern the cause of the abnormal response and to ensure that further operation is in accordance with a "zero effect" policy.

Figure 2:
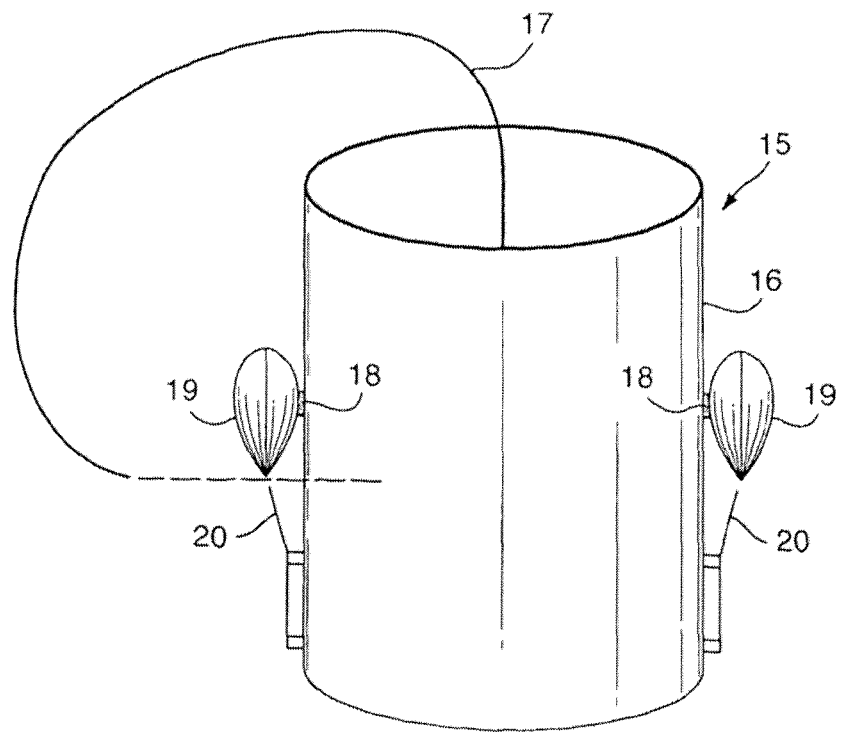

Embodiments of the invention will now be described with reference to the accompanying drawings, in which:

FIG. 1 is a schematic drawing of a biosensor unit according to an embodiment of the invention; and FIG. 2 is a schematic drawing of a biosensor unit according to an alternative embodiment of the invention which is adapted to simultaneously monitor the growth rate of a plurality of sessile organisms.

Referring to FIG. 1 there is shown a biosensor unit 1 comprising a water pervious cage 2 having plugs 3, 4 for energy and data transmissions to a sensor unit (not shown) into which the biosensor unit may be reversibly inserted.

Within biosensor unit 1 are disposed a He—Ne laser source 5, CCD light detector 6 and a blade 7. The laser source is arranged such that the beam it generates is aligned to pass immediately adjacent the edge of blade 7.

Also within biosensor unit 1 are disposed two parallel threaded tracks 8 carrying between them a fixed beam stop 9 and a mobile carriage 10. Carriage 10 is attached to a drive motor 11 operation of which causes the carriage to move towards or away from blade 7. Carriage 10 is provided with position location means (not shown) which provide a data signal indicating the relative spacing between the carriage and the blade. On carriage 10 is mounted, using adhesive 12, a sessile organism 13, e.g. a mussel, scallop or clam, with the growing edge of the shell tip pointing towards blade 7. Laser source 5, light detector 6 and drive motor 11 are provided with power and data transmission leads 14 to plugs 3 and 4.

In operation, motor 11 is engaged to draw sessile organism 13 towards blade 7 until a predetermined light diffraction pattern (i.e. one having readily discernible dark and light spots) is detected by detector 6. The average distance (d) between adjacent spots in the diffraction pattern is inversely proportional to the width of the slit (a), which can be calculated from the formula $a = \lambda \cdot s / d$, where s is the vertical distance from the slit to the diffraction pattern and $\lambda$ is the wavelength of the laser light.

After a set period of time (e.g. 24 hours), a further diffraction pattern is detected by detector 6 and used to calculate the width of the slit. The reduction in slit width provides an indication of the apical growth of the sessile organism 13. Such measurements will generally be repeated over a period of several days (or, as appropriate, several months) until the apical tip of the sessile organism 13 is almost touching blade 7 (i.e. when the diffraction pattern is almost diminished). At that point, motor 11 is engaged to draw sessile organism 13 away from blade 7 until an optimum diffraction pattern is once again obtained. The process may then be repeated to further monitor the growth rate of the sessile organism 13.

In an exemplary application of the embodiment set out above, the shell growth of mussels is monitored. The apparatus is set up to measure diffraction patterns over a range of slit apertures of 100-900 μm but to re-enlarge the aperture by moving the mussel carrier when the slit has been reduced to 200 μm. Under normal conditions in the summer with ample food (algae) in the in the water typical shell growth is of the order of 50 μm/day although can be as high as 100 μm/day. The aperture is typically re-enlarged on a weekly basis. In winter shell growth can be less than 1 μm/day and so adjustment needs only to be made at two-monthly intervals.

Referring to FIG. 2 there is shown a biosensor unit 15 in accordance with a second embodiment of the invention. In this embodiment the biosensor unit comprises a water impervious cylinder 16 having disposed therein a sensor unit (not shown) comprising a light detector. Biosensor unit 15 includes an optic fibre 17 connected to a source of laser light (not shown) positioned within the cylinder 16. Mounted on the outer surface of the cylinder 16, using adhesive 18, are a plurality of sessile organisms 19 and a plurality of plastic tabs 20. Each sessile organism 20 is mounted such that the growing edge of its shell tip is pointing towards a plastic tab 20. The optical fibre and detector may be manipulated such that the laser beam is aligned to impinge on the gap between the edge of the plastic tab 20 and the tip of the organism. The corresponding diffraction pattern is recorded. The laser-detector arrangement is then indexed round to the next organism to measure that gap. Of course the organisms could be moved (by rotating the cylinder) or each organism could be provided with its own detector.

The invention claimed is:

1. A method of monitoring the effect of pollution in an aquatic mass, said method comprising disposing in said aquatic mass a biosensor unit containing a living sessile organism which exhibits apical growth and which is bound to a carrier, directing an electromagnetic beam towards a corresponding detector contained in the biosensor unit and between an edge and the apical tip of said sessile organism whereby to produce a diffraction pattern, detecting said diffraction pattern using said detector and monitoring a change in said diffraction pattern over time which is indicative of the natural growth of the apical tip of said organism.

2. The method of claim 1 further comprising generating said electromagnetic beam from a monochromatic coherent light source.

3. The method of claim 2 wherein said light source comprises a laser.

4. The method of claim 1 further comprising moving the carrier and edge relative to one another to re-enlarge the gap between the tip of the organism and the edge.

5. The method of claim 4 further comprising initially disposing the apical tip of the sessile organism at a pre-determined distance from the edge such that the resulting slit provides a predetermined diffraction pattern.

6. The method of claim 4 further comprising moving said edge or carrier automatically.

7. The method of claim 4 further comprising determining a distance moved by the carrier or edge.

8. The method of claim 1 further comprising monitoring apical tip growth at regular intervals.

9. The method of claim 1 further comprising passing said radiation through a lens.

10. The method of claim 1 further comprising simultaneously or sequentially carrying out measurements of apical tip growth in plurality of sessile organisms from the same species.

11. The method of claim 10 further comprising bringing a radiation-and-detector arrangement into successive mutual alignment with each of a plurality of organisms.

12. The method of claim 1 further comprising transmitting data to a remote computer.

13. The method of claim 12 wherein said remote computer is configured to issue a pollution alert if said data indicate growth below a predetermined threshold.

\* \* \* \* \*

UNITED STATES PATENT AND TRADEMARK OFFICE
CERTIFICATE OF CORRECTION

PATENT NO.        : 9,057,717 B2
APPLICATION NO.   : 13/512285
DATED             : June 16, 2015
INVENTOR(S)       : Andersen Page 1 of 1

It is certified that error appears in the above-identified patent and that said Letters Patent is hereby corrected as shown below:

In the specification
In column 4, line 23,
replace "(COD)"
with "(CCD)"

Signed and Sealed this
Fifteenth Day of March, 2016

Michelle K. Lee
*Director of the United States Patent and Trademark Office*